United States Patent
Cauche et al.

(10) Patent No.: US 12,220,144 B2
(45) Date of Patent: Feb. 11, 2025

(54) METHOD FOR SHEARING TISSUE

(71) Applicant: UNIVERSITE LIBRE DE BRUXELLES, Brussels (BE)

(72) Inventors: Nicolas Cauche, Brussels (BE); Orianne Bastin, Lasnes (BE); Jacques Deviere, Bornival (BE); Sonia Dugardeyn, Bornival (BE); Ricardo Rio Tinto, Lisbon (PT); Daniel Blero, La Hulpe (BE); Cécilia Delattre, Molenbeek Saint Jean (BE); François Huberland, Ixelles (BE); Alain Delchambre, Brussels (BE)

(73) Assignee: UNIVERSITE LIBRE DE BRUXELLES, Brussels (BE)

( * ) Notice: Subject to any disclaimer, the term of this patent is extended or adjusted under 35 U.S.C. 154(b) by 182 days.

(21) Appl. No.: 17/748,940

(22) Filed: May 19, 2022

(65) Prior Publication Data

US 2022/0273330 A1    Sep. 1, 2022

Related U.S. Application Data

(63) Continuation of application No. 16/489,584, filed as application No. PCT/EP2018/055106 on Mar. 1, 2018, now Pat. No. 11,337,722.

(30) Foreign Application Priority Data

Mar. 1, 2017 (EP) .................................... 17158646

(51) Int. Cl.
A61B 17/3205    (2006.01)
A61B 17/06    (2006.01)
(Continued)

(52) U.S. Cl.
CPC .. *A61B 17/32056* (2013.01); *A61B 17/06166* (2013.01); *A61B 17/1114* (2013.01);
(Continued)

(58) Field of Classification Search
CPC .... A61B 17/32056; A61B 2017/32006; A61B 2017/32096; A61B 17/3209;
(Continued)

(56) References Cited

U.S. PATENT DOCUMENTS 6,648,903 B1 * 11/2003 Pierson, III ........ A61B 17/0401
606/232
2005/0182429 A1 * 8/2005 Yamanouchi .... A61B 17/12022
606/153
(Continued)

FOREIGN PATENT DOCUMENTS

WO    WO-2014055193 A1 * 4/2014 ......... A61B 17/1114

*Primary Examiner* — Brigid K Byrd
(74) *Attorney, Agent, or Firm* — Kolitch Romano Dascenzo Gates LLC (57) ABSTRACT

A method is described for shearing a tissue wall between a first cavity and an adjacent second cavity in a human or animal body. The tissue wall has a periphery forming an edge of an opening between the first cavity and the second cavity. A first member is placed into the first cavity, such that the first member is adjacent the wall. A second member is placed in the second cavity, proximate the first member. The first and second members have materials which magnetically attract one another. The first member and the second member are placed such that there is magnetic attraction between the first member and the second member through the wall and thereby compress an overlapping portion of the wall to create pressure necrosis. The first member and the second member are connected by a thread, wherein the thread extends over the edge of the opening.

20 Claims, 10 Drawing Sheets

(51) Int. Cl.
    *A61B 17/11*     (2006.01)
    *A61B 17/3209*     (2006.01)
    *F16H 7/08*     (2006.01)
    *A61B 17/00*     (2006.01)
    *A61B 17/04*     (2006.01)
    *A61B 17/32*     (2006.01)

(52) U.S. Cl.
    CPC ........... *A61B 17/3209* (2013.01); *F16H 7/08* (2013.01); *A61B 2017/00871* (2013.01); *A61B 2017/00876* (2013.01); *A61B 2017/0496* (2013.01); *A61B 2017/0618* (2013.01); *A61B 2017/1117* (2013.01); *A61B 2017/1139* (2013.01); *A61B 2017/32006* (2013.01); *A61B 2017/32096* (2013.01); *F16H 2007/081* (2013.01)

(58) Field of Classification Search
    CPC .. A61B 2017/00876; A61B 2017/0472; A61B 2017/0496; A61B 17/0469; A61B 17/0482; A61B 17/0483; A61B 2017/0618; A61B 2017/00818–00827; A61B 2017/00278; A61B 17/122–1285; A61B 17/1114–2017/1117; A61B 17/1139; A61B 17/221–2017/2212

See application file for complete search history.

(56) References Cited

U.S. PATENT DOCUMENTS

| | | | |
|---|---|---|---|
| 2008/0200934 A1* | 8/2008 | Fox | A61B 17/1114 606/153 |
| 2008/0300618 A1* | 12/2008 | Gertner | A61F 5/003 606/192 |
| 2009/0024144 A1* | 1/2009 | Zeiner | A61F 5/0079 606/142 |
| 2011/0009886 A1* | 1/2011 | Gagner | A61B 17/1114 606/153 |
| 2013/0053874 A1* | 2/2013 | Ekvall | A61B 17/12013 606/157 |
| 2016/0324527 A1* | 11/2016 | Thompson | A61B 17/12009 |
| 2018/0193050 A1* | 7/2018 | Hawkins | A61B 17/0644 |
| 2018/0214152 A1* | 8/2018 | Bakos | A61B 17/06 |

* cited by examiner

Top view

FIG 7A  FIG 8A  FIG 9A  FIG 10A

Front view

FIG 7B  FIG 8B  FIG 9B  FIG 10B

Side view

FIG 7C  FIG 8C  FIG 9C  FIG 10C

Top view

Front view

Side view

METHOD FOR SHEARING TISSUE

FIELD

The present disclosure is related to assemblies and methods for creating pressure necrosis of wall portions of internal cavities of a human or animal body, and possibly creating compression anastomosis of adjacent wall portions.

BACKGROUND ART

There exist a number of medical conditions in which a wall of an internal body cavity pouches out to form an undesired hollow protrusion, referred to as diverticulum. Diverticulum can occur in various body cavities, such as though not limited to the gastrointestinal tract (oesophagus, intestine, colon), the bladder and the heart. In some instances of diverticulum, fluids or solid substances such as food present in the cavity can get trapped in the pouch (diverticulum) and remain stagnant for a prolonged period, eventually leading to infection. In other instances, fluid or solid substances get blocked, and cannot pursue their natural course. Current treatment techniques involve endoscopic stapling of the diverticulum. In other medical conditions, there is a need to open or adapt a septum between two cavities.

On the other hand, methods and apparatuses for creating compression anastomosis between walls of adjacent body cavities and related pressure necrosis are known from EP 0754434 to Cook Incorporated, 22 Jan. 1997 and WO 2012/007052 to Ethicon Endo-Surgery Inc., 19 Jan. 2012. Magnets are placed in each of the two body cavities, which attract one another and attract adjacent cavity walls being interposed between the magnets. The magnets will strongly compress the wall tissues trapped between them leading to a cut-off from blood supply, which causes necrosis of the tissue between the magnets and anastomosis of the surrounding tissue.

From U.S. Pat. No. 8,828,032 to GI Windows Inc., 9 Sep. 2014, it is known to provide a train of self-assembling magnets which yield a larger surface on self-assembly than the size of any single magnet component. These structures are useful when a larger opening must be created between adjacent body cavities. The train of self-assembling magnets can be delivered successively through a needle. The magnets may be preloaded with a suture allowing the proximal and distal magnet elements to be tied to one another. The suture continues to run from the needle as the needle is retracted through the separating wall between the cavities and is attached to the second train of magnets, thereby linking the self-assembly magnet structures in both cavities through the separating wall. One drawback of the above self-assembling magnet trains is that the number of components increases with an increase in the size of the opening that one wishes to create, and therefore the difficulty of assembling such large number of components increases proportionally.

It is therefore desirable to provide a method and an assembly or device which allow for creating a lesion between adjacent cavities with a same difficulty level of implementation irrespective of the size of the lesion one wishes to create. It is desirable to provide such methods and assemblies which overcome the above drawbacks. It is desirable to provide such methods and devices allowing for effectively forming an opening through a tissue wall, in particular tissue walls separating adjacent bodily cavities and lumens, in particular through pressure necrosis and/or anastomosis. It is desirable to provide such methods and devices allowing for creating a lesion, such as tissue shearing, with less trauma, and less complexity. It is desirable to provide such methods and devices allowing for effectively treating diverticulum and/or for effectively and easily performing anastomosis, in particular along or within the gastrointestinal tract.

SUMMARY

Some aspects described further herein therefore provide a device or assembly as set out in the appended claims. The device or assembly comprises a first member comprising a first material, a second member comprising a second material and a thread connected to the first member and to the second member. The first and second materials show magnetic attraction between one another. The device or assembly enables to perform methods as described herein. In some aspects described herein, the device of assembly comprises means for pulling the thread. The means for pulling the thread is advantageously configured to apply a tension on the thread between the first member and the second member. Advantageously, the means for pulling the thread is configured to reduce a length of the thread between the first member and the second member.

When the thread of the above devices or assemblies are operating within the human or animal bodies to shear tissue, the means for pulling the thread allow for applying an additional force/pressure on the tissue by the thread, so that tissue becomes necrotic due to prolonged action of the pressure and can be sheared more effectively, and with increased safety, e.g. reducing risk of infections.

According to a first aspect, one or both of the first member and the second member are each attached to the thread at a fixed position along the thread.

According to a second aspect, at least one of the first and second members are connected to the thread so as to be able to slide along the thread. By way of example, the device or assembly comprises a third member connected to the thread at one end thereof. The first member can be attached to the other end of the thread. The third member can perform as the means for pulling the thread, e.g. it can comprise a mass configured to pull the thread by gravity.

According to a third aspect, the third member is interposed between the first member and the second member. Advantageously, the third member comprises a material showing magnetic attraction to one or both of the first member and the second member. Alternatively, or in addition, a plurality of third members are connected to the thread at spaced apart intervals from one another between the first member and the second member. The plurality of third members advantageously show magnetic attraction to one or both of the first member and the second member, so that they progressively pull the thread towards the first or second member as the tissue is being sheared.

According to a fourth aspect, the device or assembly comprises a thread winding system (traction system) configured to pull the thread in order to maintain a tension on the thread between the first member and the second member.

The first to fourth aspects, and any aspects described further herein can be combined in any suitable combination to provide improved effects. By way of example, the fourth aspect is an implementation example of the second aspect as described above.

Some aspects described further herein therefore aim to provide a method for shearing tissue by means of the devices and assemblies described herein. Tissue shearing can be provided alone or in combination with other operations, such as though not limited to pressure necrosis and compression anastomosis. In one aspect, a method is described for creating pressure necrosis of a tissue wall between a pouch and an adjacent cavity in a human or animal body, and possibly anastomosis of surrounding tissue. The pouch advantageously opens into the cavity. The tissue wall hence comprises a periphery forming an edge of the opening between the pouch and the cavity. These conditions can refer to diverticulum, such as though not limited to Zenker's diverticulum, and epiphrenic diverticulum and present methods advantageously allow for treating these.

According to the method, a first member is placed into the pouch, such that the first member is adjacent the tissue wall. A second member is placed in the cavity and proximate the first member. The first member and the second member comprise materials which magnetically attract one another. The first member and the second member are placed such that there is magnetic attraction between the first member and the second member through the wall. Due to the magnetic attraction force, the first member and the second member compress a portion of the wall overlapping the first member and the second member for a prolonged time period, which creates pressure necrosis of that overlapping wall portion. A thread extends between the first member and the second member and is connected thereto, and extends over the edge to form a loop over the wall.

The tissue compressed between the first member and the second member becomes necrotic, and collapses, thereby forming an opening through the wall. Advantageously, due to the means for pulling the thread, a continuing pressure can be applied by the thread on the tissue, to create a local necrosis of the tissue, which aids in tissue shearing by the thread, and renders it more effective and safer. The first member and the second member, which remain attached to one another due to the magnetic attraction force, separate from the tissue wall and become suspended from the thread. The first and second members and the thread form a closed loop around the tissue wall, enclosing a portion of tissue between the edge and the freshly formed necrotic opening. Due to their weight, the first and second members now may further pull on the thread loop, such as in the direction of gravity. As the thread is supported by the tissue edge, the tension in the thread caused by the weight of the first and second members may further assist shearing the tissue from the edge to the necrotic opening. As a result, the separating wall between the pouch and the cavity can be opened substantially over the entire height of the wall without having recourse to large magnets or large magnet assemblies. As a further result, the pouch is now completely open to the cavity, which may prevent infections due to stagnancy in the pouch or create a preferential passage for liquid and solid substances, e.g. through the GI tract. It will be convenient to note that the tension in the thread by the means for pulling the thread on the one hand and by gravity due to the suspended masses of the first and second members on the other hand, may act simultaneously to provide improved effects.

Some aspects described further herein aim to provide a method of creating compression anastomosis and/or pressure necrosis between one or more adjacent tissues. Each of the tissues forms a wall of one of adjacent cavities of a human or animal body. These cavities can e.g. form part of the gastrointestinal tract. Possible anastomosis applications include, but are not limited to gastrojejunal anastomosis and jejuno-jejunal anastomosis. According to the method, a first member and a second member are placed in a first one of the adjacent cavities, proximate a first one of the walls, e.g. through an endoscopic delivery device guided to the cavity. The first member and the second member are spaced apart and connected to a first thread. A third member and a fourth member are placed in a second one of the adjacent cavities and proximate a second one of the walls. The third member and the fourth member are connected to a second thread and are placed in correspondence of a respective one of the first member and the second member. The first, second, third and fourth members comprise materials which magnetically attract one another through the adjacent tissues to create pressure necrosis of an overlapping portion of the wall.

Due to pressure necrosis, portions of the adjacent tissues overlapping the first member and overlapping the second member will collapse, and form necrotic openings through the tissues. The tissues adjacent the necrotic openings will anastomose. The magnetic members fall through the necrotic opening and remain suspended by the threads, which now form a loop with the first to fourth members. The loop of threads and magnetic members are supported by the tissue portions between the necrotic openings. The members will pull on the thread due to their weight and start shearing the tissue portions until a lesion extending between the two necrotic openings is formed. As a result, a large opening can be created between adjacent body cavities in a simple way.

BRIEF DESCRIPTION OF THE DRAWINGS

Aspects of the invention will now be described in more detail with reference to the appended drawings, which are illustrative and non-limiting, and wherein same reference numerals illustrate same features.

FIG. 3A illustrates the situation in FIG. 2C in a first of two other views;

specifically a perspective cut-out view of the lumen of the GI tract.

FIG. 23A represents a perspective view of the device.

FIG. 23B illustrates a second of three views of an alternative embodiment of the devices of FIGS. 22A-B, wherein the magnet is arranged differently; specifically FIG. 23B represents a cross sectional view of the second member, and shows the annular magnet and the thread winding system including a pulley for winding the thread.

FIG. 23C illustrates a third of three views of an alternative embodiment of the devices of FIGS. 22A-B, wherein the magnet is arranged differently; specifically FIG. 23C represents a perspective partial cut-out view of the second member, and shows the annular magnet and the thread winding system including a pulley for winding the thread.

It will be convenient to note that some parts in the figures have been drawn in transparency in order to uncover interior components.

DETAILED DESCRIPTION

Figure 1:
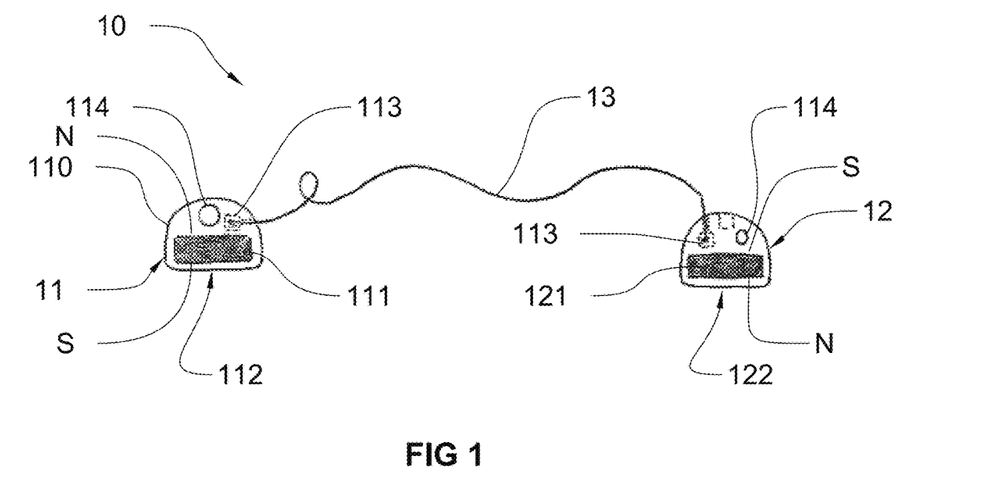
FIG. 1 illustrates a device or assembly for creating pressure necrosis of a tissue interposed between opposing magnets followed by shearing of the tissue by a thread.

Referring to FIG. 1, a device 10 for pressure necrosis and tissue shearing according to one aspect comprises a first member 11 and a second member 12 connected to one another by a thread 13. Each of the first member 11 and second member 12 can comprise a generally dome shaped housing 110 advantageously made of a biocompatible material. The housing 110 encapsulates a material 111, 121 respectively. The materials 111, 121 encapsulated within the respective members 11, 12 show magnetic attraction to one another. Advantageously, both materials 111 and 121 can be permanent magnets. Alternatively, one material can be a permanent magnet, and the other one a material which is magnetically attracted to the permanent magnet, such as though not limited to a ferromagnetic material, e.g. an iron alloy. Each of the first member 11 and the second member comprises a generally planar surface of contact 112, 122 respectively, advantageously forming a bottom of the housing 110. The materials 111 and 121 advantageously have magnetic properties such that they show magnetic attraction when the first member and the second member are placed with their surface of contact 112, 122 against each other, e.g. through suitable orientation of the magnetic poles N and S of the permanent magnets within the housing 110. In use, therefore, the first and second members will be disposed in such a manner that the surfaces of contact 112, 122 are in facing relationship. Each of the first and second member further comprises a point of attachment 113 at which the thread 13 is connected to the respective member. The thread connection at 113 is advantageously a fixed connection, e.g. the thread 13 is fixedly secured, such as through tying or potting to the member. Each member 11, 12 may further comprise a suitable structure for facilitating handling of the member, e.g. an eye 114, allowing an endoscopic tool for engaging the respective member.

As a surprising effect, the device 10 allows for creating an opening through a tissue wall separating two body cavities. The opening is larger than the size of any of the first member 11 and the second member 12. To this end, the members 11, 12 comprising the magnets 111, 121 are used, in a first step, for compressing tissue between oppositely arranged magnetically attracting members thereby causing pressure necrosis. Subsequently, in a second step, the necrotic tissue collapses and forms an opening. The members 11, 12 lack support by the tissue and will fall through the opening created by necrosis. The members 11, 12 become suspended by thread 13 and will pull on the thread 13 due to gravity. The thread 13, supported by the tissue, will start shearing the tissue to create a larger opening.

Figure 2A:
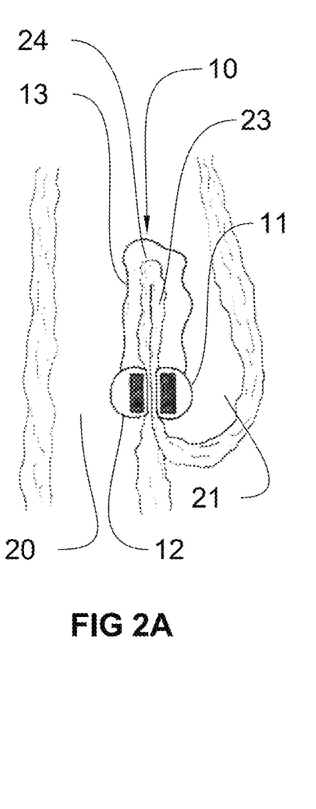
FIG. 2A represents a cross section of a lumen of the gastrointestinal (GI) tract of a human body along a sagittal plane and illustrates initial placement of the device of FIG. 1 in performing pressure necrosis and tissue shearing between the lumen and an adjacent pouch.
Figure 2B:
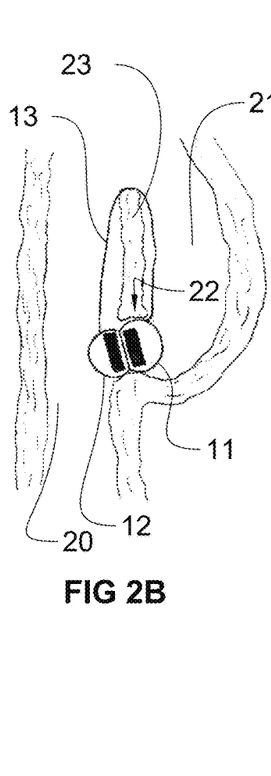
FIG. 2B illustrates an opening through the wall separating the pouch from the lumen and which is formed by pressure necrosis.
Figure 2C:
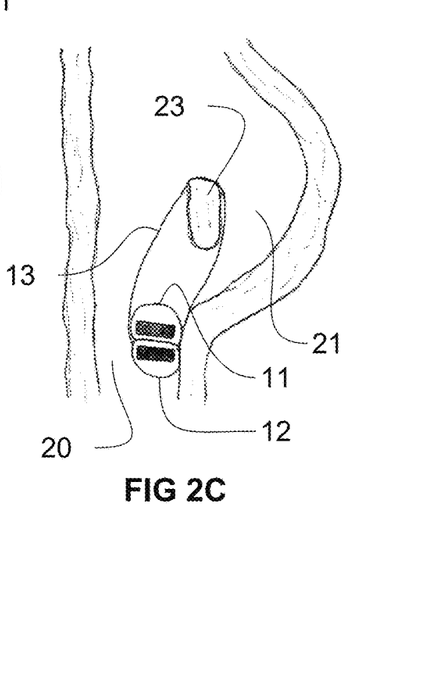
FIG. 2C illustrates further shearing of the separating wall by the thread.

A first possible application is shown in FIGS. 2A-C and relates to treatment of diverticulum, such as though not limited to Zenker's diverticulum, which is a pouch 21 protruding from a lumen of the GI tract 20. In the particular case of Zenker's diverticulum, the lumen 20 is the hypopharynx. Referring to FIG. 2A, the device 10 is introduced into the lumen 20 and the first member 11 placed in the pouch 21 while the second member 12 placed in the lumen 20 at a corresponding location. The device 10 can be introduced by any suitable endoscopic means. Since the pouch 21 is open towards the lumen 20, a delivery device, such as an endoscope with suitable system for engaging and positioning the members 11, 12, e.g. a grasper, forceps or specific catheter, can be guided to the pouch 21 to place the first member 11. No tissue needs to be pierced in order to place member 11. The same endoscope or another endoscope can be guided to the adjacent lumen 20 to place the second member 12. It is alternatively possible to place the second member 12 first, and to place the first member 11 subsequently. The thread 13 is either connected to the two members 11 and 12 prior to loading the device 10 in the endoscope, or may be connected to either or both members upon placement. Advantageously, the thread 13 connecting the two members 11 and 12 does not pass through the tissue wall 23, but forms a loop over the periphery 24 of the tissue wall. The placement of the members can be guided with endoscopic ultrasound and/or fluoroscopy which are procedures well-known to persons skilled in the art of endoscopic procedures.

Figure 3A:
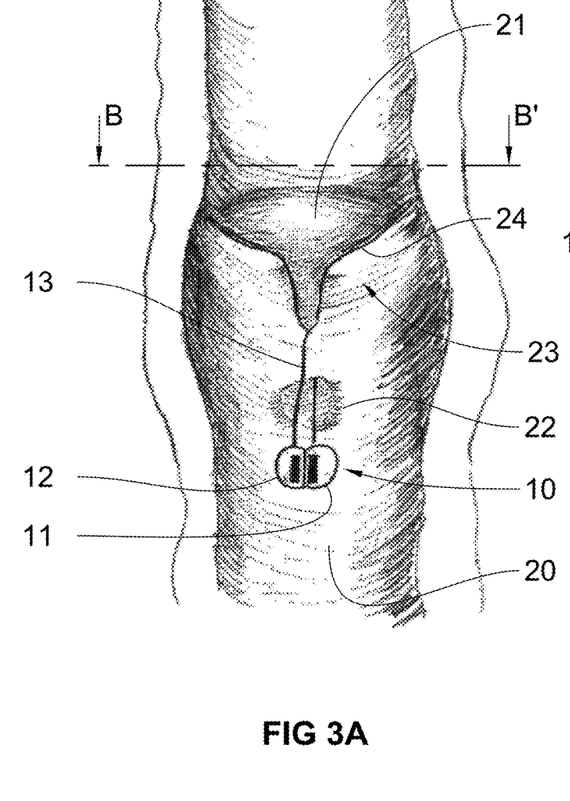
Figure 3B:
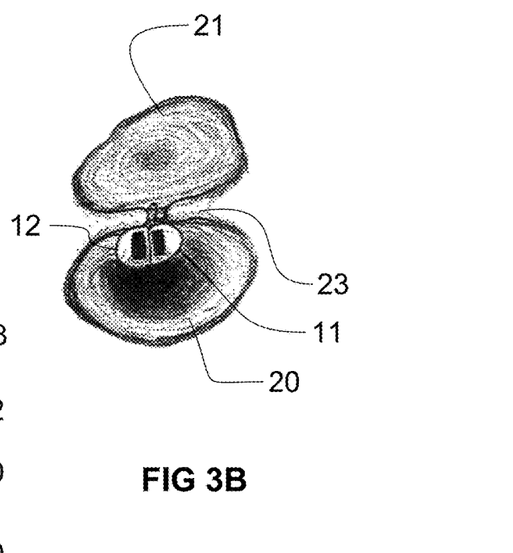
FIG. 3B illustrates the situation in FIG. 2C in a second of two other views; specifically a view of the hollow parts of the lumen and the adjacent pouch as seen from section plane B-B' in a downwards direction as indicated by the arrows of FIG. 3A.

Referring to FIG. 2B, due to the magnetic attraction between the members 11 and 12, the tissue wall 23 gets trapped between the two members and is compressed. By suitable selection of the magnetic attraction force between the magnets 111 and 121, a compression pressure larger than 5 mm Hg can be created, which is sufficient for stopping blood supply to the trapped tissue and hence causing necrosis of the tissue within a few days. The necrotic tissue trapped between the members 11 and 12 collapses and frees the members 11 and 12 which remain attached to one another and suspended on the thread 13. The first and second members and the thread now form a closed loop around the tissue wall 23, enclosing that portion of tissue interposed between the periphery 24 and the freshly formed necrotic opening. Due to their weight, the members 11 and 12 now pull on the thread loop 13 in the direction of gravity. Referring to FIG. 2C, the thread 13 is now supported by the periphery 24 of the tissue wall and the tension in the thread 13 caused by the weight of the members 11 and 12 will start shearing the tissue from the periphery 24 until the initial opening 22 formed by necrosis is reached. The action of the thread 13 shearing the tissue wall 23 is represented in FIGS. 3A-B from other viewing directions. By so doing, a lesion extending over the entire depth of the pouch 21 can be created without requiring recourse to larger structures and without requiring specific delivery devices.

Figure 4:
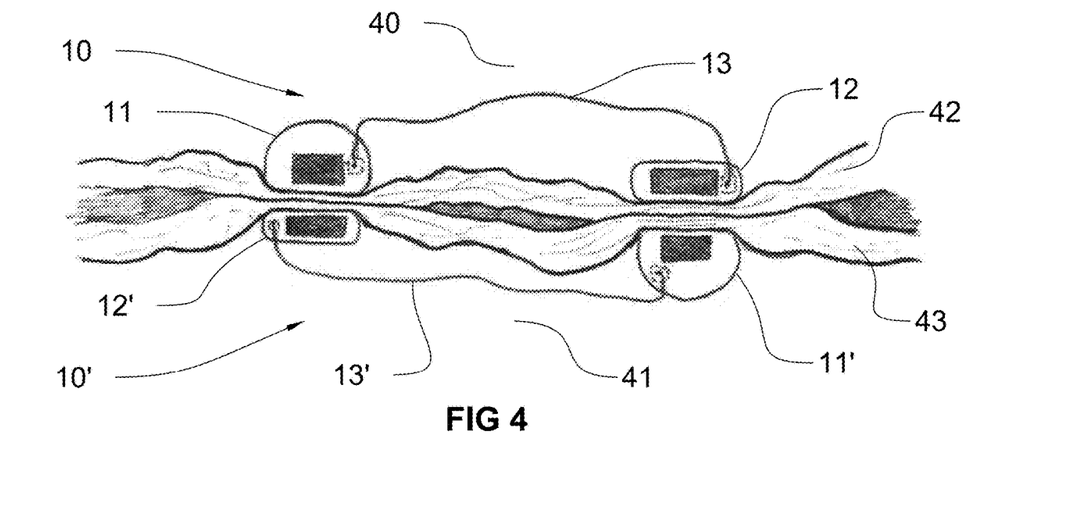
FIG. 4 illustrates another application of the device of FIG. 1 for creating an opening between two adjacent cavities.

The example described above is just one possibility of how device 10 can be used. Referring to FIG. 4, with two such devices 10 and 10', with each one device placed in one of two adjacent cavities 40, 41, a lesion can be created extending over the distance by which the first member 11 and the second member 12 are spaced apart. The magnetically attracting members 11 and 12' of respective devices 10, 10' are placed in correspondence, each in the respective cavity. Portions of the tissue walls 42 and 43 of each respective cavity 40, 41 overlapping the members 11 and 12' are compressed. Likewise, the other members 12 and 11', which also magnetically attract each other, are placed in correspondence, each in the respective cavity at a location spaced apart from the members 11 and 12'. Portions of the tissue walls 42 and 43 overlapping the members 12 and 11' are compressed. Members 11 and 12 are spaced apart from each other, such as by a distance of at least 40 mm, advantageously at least 50 mm to enable making a larger lesion. The tissue trapped between members 11 and 12' on the one hand and between members 12 and 11' on the other hand will become necrotic and collapse, which will free the members towards one cavity 40 or the other one 41. Either thread 13 or 13' will be pulled by the freed member couples 11-12' and 12-11' in the direction of gravity, which will shear the tissue in between the openings formed. It will be convenient to note that also in the case of FIG. 4, no puncture or piercing through the tissue wall is required for initial placement of the devices 10 and 10', as long as both cavities 40 and 41 are accessible. A configuration as in FIG. 4 may be useful for creating gastrojejunal anastomosis or jejuno-jejunal anastomosis.

It will be convenient to note that devices and assemblies described herein advantageously allow to perform tissue shearing assisted by pressure necrosis and/or compression anastomosis.

Figure 5:
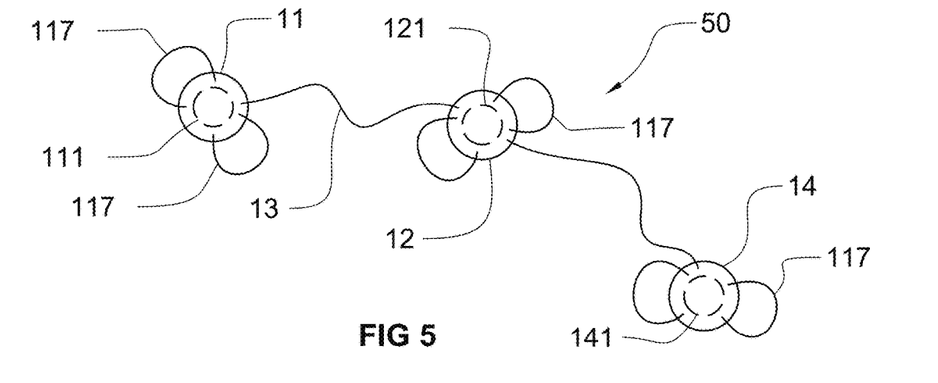
FIG. 5 illustrates a device or assembly for creating pressure necrosis in an application as shown in FIG. 4, comprising three magnetic members connected to a thread.
Figure 6A:
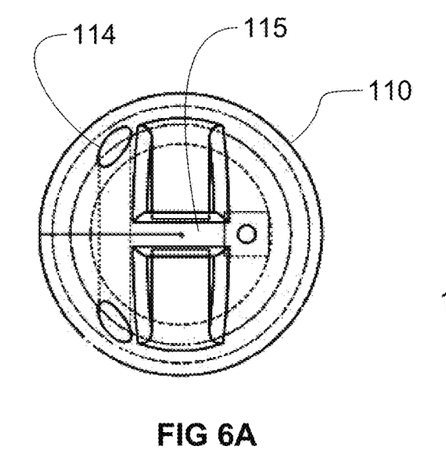
FIG. 6A illustrates a first of four different views of a possible housing of a member of the device or assembly of FIG. 1 or FIG. 5; specifically a top view of the housing.
Figure 6B:
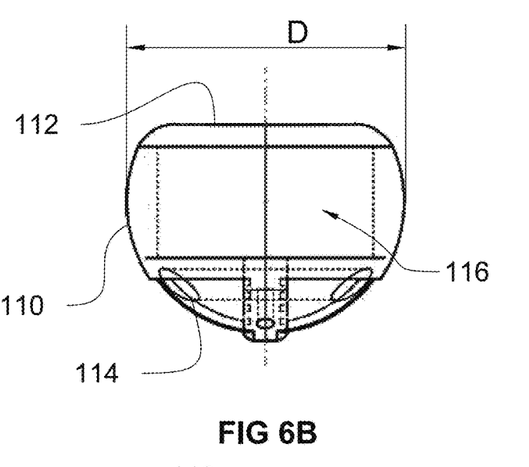
FIG. 6B illustrates a second of four different views of a possible housing of a member of the device or assembly of FIG. 1 or FIG. 5; specifically a side view taken along a first perpendicular direction.
Figure 6C:
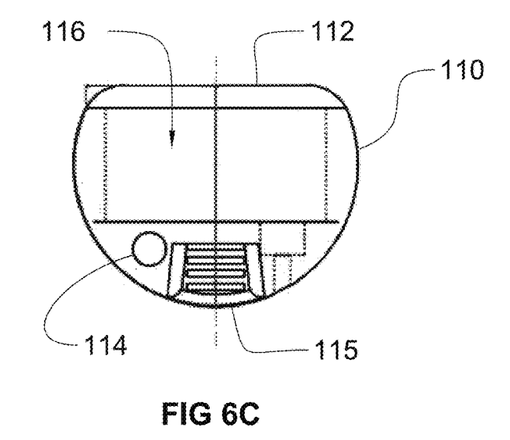
FIG. 6C illustrates a third of four different views of a possible housing of a member of the device or assembly of FIG. 1 or FIG. 5; specifically a side view taken along a second perpendicular direction.
Figure 6D:
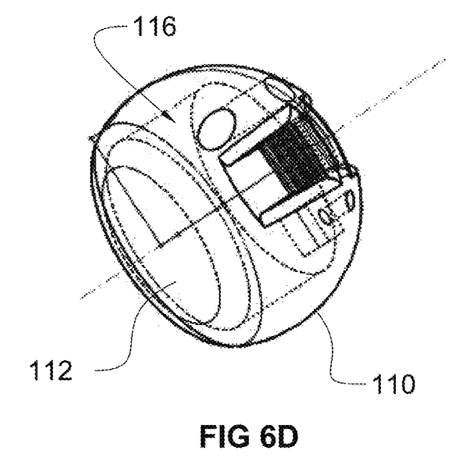
FIG. 6D illustrates a fourth of four different views of a possible housing of a member of the device or assembly of FIG. 1 or FIG. 5; specifically a perspective view of the housing.
Figure 7A:
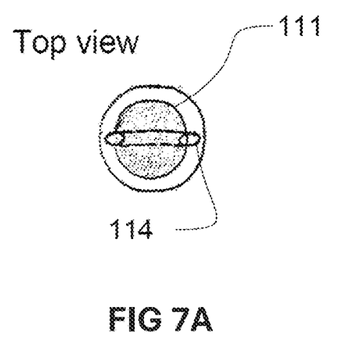
FIGS. 7A-7C illustrate a top view, front view, and side view of the magnetic members of devices or assemblies of FIG. 1 or FIG. 5 having a first of four different orientations for the engagement hole; specifically the engagement hole arranged centrally and extending parallel to the surface of contact.
Figure 7B:
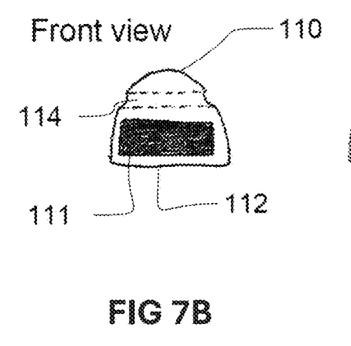
Figure 7C:
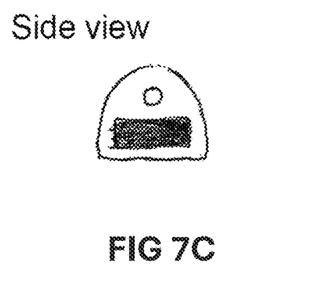

Even though the devices 10 and 10' in FIG. 4 are shown to comprise two magnetic members 11, 12 and 11', 12' each, it will be clear that device configurations comprising more than two members, such as three members or four members connected by a thread are similarly applicable. By way of example, device 50 shown in FIG. 5 comprises three members 11, 12 and 14 connected by thread 13. Two such devices 50 can be used in the same way as the example shown in FIG. 4, each device being placed in a different one of the adjacent cavities 40 and 41, as with the devices 10 and 10'. The third member 14 may comprise its proper magnet 141 or magnetically active material.

The shape of the housing 110 of the members 11, 12 and possibly 14, and the shape of the magnets or magnetically active materials 111, 121 as well as of the surface of contact 112, 122 is not particularly limited. Suitable shapes and configurations may be chosen depending on any particular application. By way of example, instead of dome-shaped, such housing may be cylindrical, advantageously with planar top and bottom base. There is no preference for using the top or the bottom as surface of contact in the latter case.

Each member can comprise a suitable handling structure for manipulating the member. In a first example, referring to FIG. 5, the members 11, 12 and 14 can comprise one or more thread loops 117 which facilitate handling of the members by a forceps. The thread loops 117 project from the housing of the member and can be provided in addition or in alternative to other handling structures, such as the engagement eye. In another example, referring to FIGS. 6A-D, the engagement eye or hole 114, or the thread loop 117 as in FIG. 5, can be replaced by, or be supplemented with an advantageously ribbed projecting wall 115 allowing engagement by a forceps, e.g. of the types commonly used in endoscopic procedures. The magnet, or magnetically active material is received in interior and completely closed recess 116. Referring to FIGS. 7A-10C, the engagement hole 114 may be oriented parallel to the surface of contact 112, perpendicular thereto, or oblique.

Figures 8A, 9A:
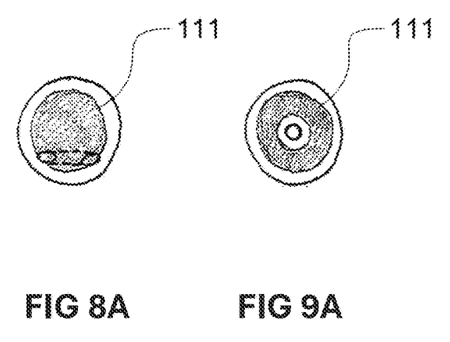
FIGS. 8A-8C illustrate a top view, front view, and side view of the magnetic members of devices or assemblies of FIG. 1 or FIG. 5 having a second of four different orientations for the engagement hole; specifically the engagement hole arranged eccentric and extending parallel to the surface of contact.
FIGS. 9A-9C illustrate a top view, front view, and side view of the magnetic members of devices or assemblies of FIG. 1 or FIG. 5 having a third of four different orientations for the engagement hole; specifically the central engagement hole extending perpendicular to the surface of contact with ring-shaped magnet surrounding the engagement hole.
Figure 8B:
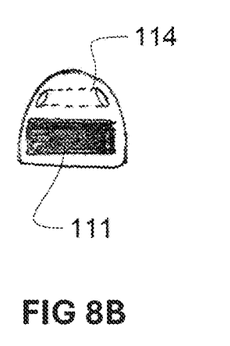
Figure 8C:
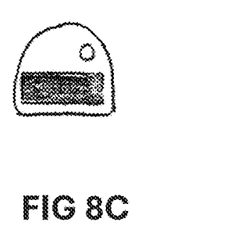
Figure 9B:
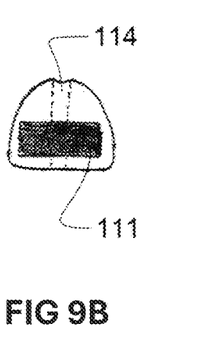
Figure 9C:
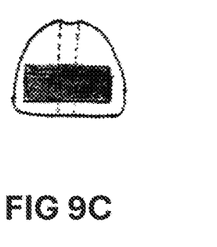
Figure 10A:
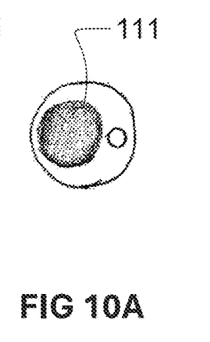
FIGS. 10A-10C illustrate a top view, front view, and side view of the magnetic members of devices or assemblies of FIG. 1 or FIG. 5 having a fourth of four different orientations for the engagement hole; specifically the engagement hole extending perpendicular to the surface of contact and arranged eccentric to the magnet.
Figure 10B:
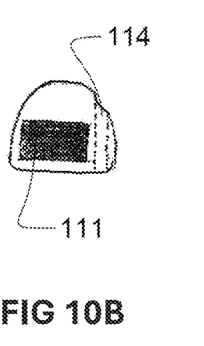
Figure 10C:
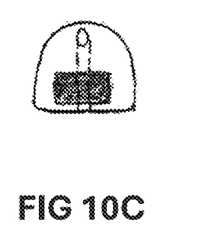
Figures 11A, 12A:
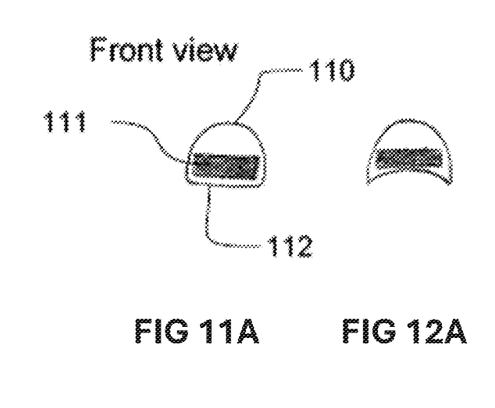
FIGS. 11A and 11B illustrate a front view and a corresponding bottom view of a first of seven different shapes of the surface of contact and housing of the magnetic members of the device of FIG. 1 or FIG. 5; specifically a planar surface of contact.
FIGS. 12A and 12B illustrate a front view and a corresponding bottom view of a second of seven different shapes of the surface of contact and housing of the magnetic members of the device of FIG. 1 or FIG. 5; specifically a concave surface of contact.
Figure 11B:
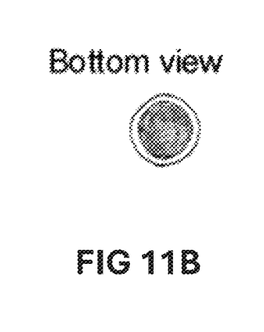
Figure 12B:
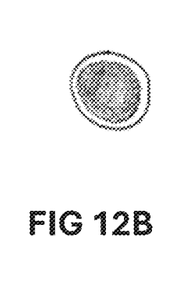
Figure 13A:
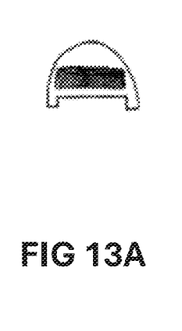
FIGS. 13A and 13B illustrate a front view and a corresponding bottom view of a third of seven different shapes of the surface of contact and housing of the magnetic members of the device of FIG. 1 or FIG. 5; specifically a planar surface of contact with protruding edge.
Figure 13B:
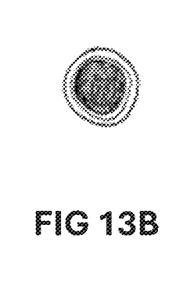
Figure 14A:
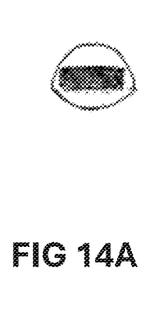
FIGS. 14A and 14B illustrate a front view and a corresponding bottom view of a fourth of seven different shapes of the surface of contact and housing of the magnetic members of the device of FIG. 1 or FIG. 5; specifically a convex surface of contact.
Figure 14B:
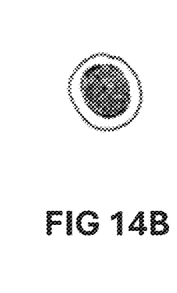
Figure 15A:
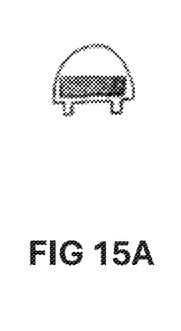
FIGS. 15A and 15B illustrate a front view and a corresponding bottom view of a fifth of seven different shapes of the surface of contact and housing of the magnetic members of the device of FIG. 1 or FIG. 5; specifically a planar surface of contact with intermediate protrusion.
Figure 15B:
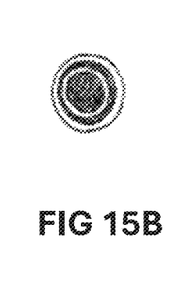
Figure 16A:
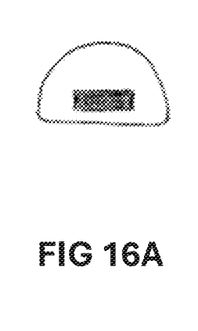
FIGS. 16A and 16B illustrate a front view and a corresponding bottom view of a sixth of seven different shapes of the surface of contact and housing of the magnetic members of the device of FIG. 1 or FIG. 5; specifically a planar surface of contact substantially larger than the size of the magnet.
Figure 16B:
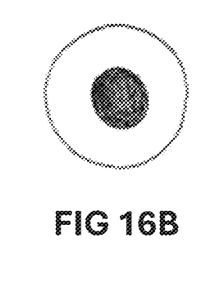
Figure 25:
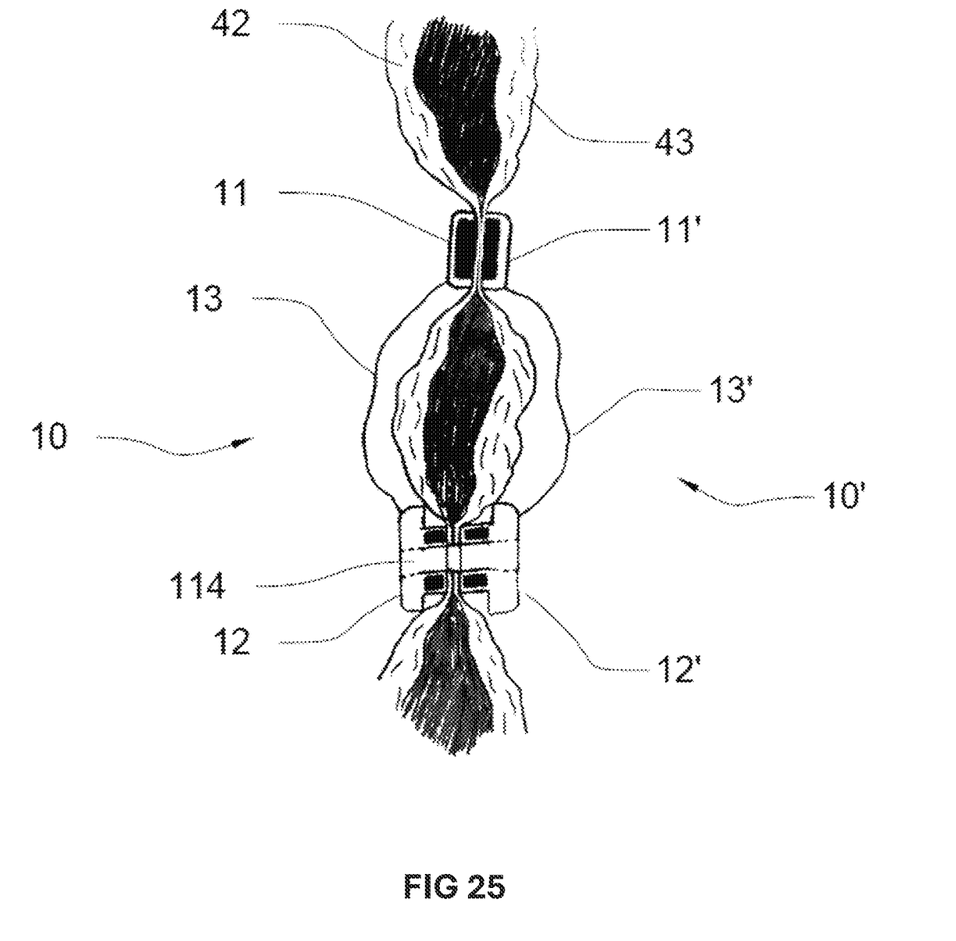
FIG. 25 illustrates an alternative to FIG. 4, in which a through passage is provided in two opposed magnetic members, in order to allow passage of a medical tool, such as a needle through the tissue.

Referring to FIGS. 9A-9C, it may be useful to provide the hole 114 as a through-hole and the magnet 111 advantageously surrounding the through-hole 114. The through-hole is advantageously arranged to traverse the surface of contact 112 of the member. One advantage of such an arrangement is shown in FIG. 25. FIG. 25 differs with respect to FIG. 4 only in the shape of the second members 12, 12' which comprise such a through-hole 114 and in which the magnets are advantageously annular surrounding the through-hole 114. Referring to FIG. 25, the through-hole 114 allows to pass a medical tool, such as a needle, through the respective member 12, 12'. Since the magnets of members 12 and 12' surround the through-hole 114, a necrotic tissue, which may be anastomosed, is created surrounding the location of the through-hole 114, allowing a needle or other tool to pass through the tissues 42 and 43 safely.

Figure 17A:
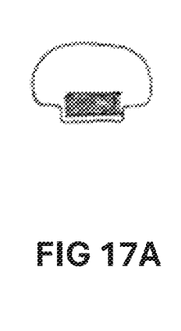
FIGS. 17A and 17B illustrate a front view and a corresponding bottom view of a seventh of seven different shapes of the surface of contact and housing of the magnetic members of the device of FIG. 1 or FIG. 5; specifically a stair stepped surface of contact.
Figure 17B:
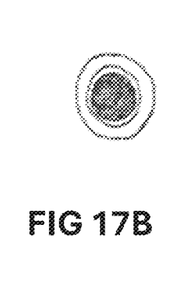
Figure 18A:
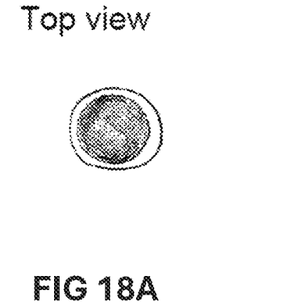
FIGS. 18A-18C illustrate a top view, front view, and corresponding side view of a first of three magnetic members of devices or assemblies of FIG. 1 or FIG. 5 having different arrangements of magnets; specifically a monolithic magnet of disc or cylindrical shape.
Figure 18B:
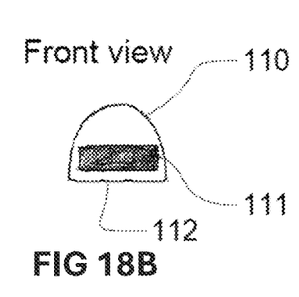
Figure 18C:
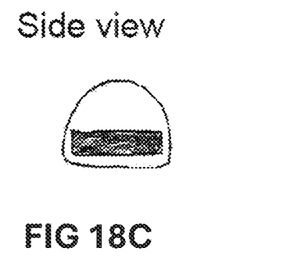
Figure 19A:
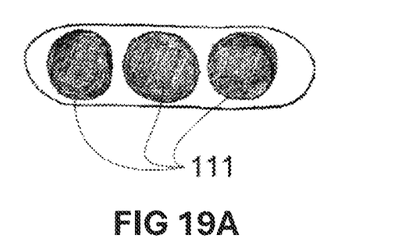
FIGS. 19A-19C illustrate a top view, front view, and corresponding side view of a second of three magnetic members of devices or assemblies of FIG. 1 or FIG. 5 having different arrangements of magnets; specifically an array of multiple disc shaped magnets.
Figure 19B:
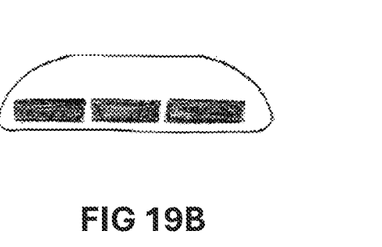
Figure 19C:
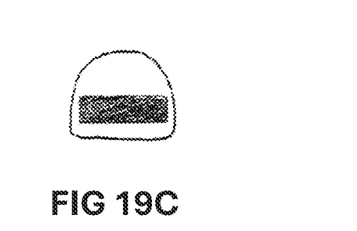
Figure 20A:
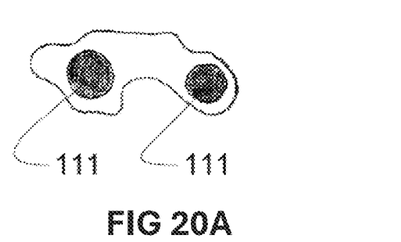
FIGS. 20A-20C illustrate a top view, front view, and corresponding side view of a third of three magnetic members of devices or assemblies of FIG. 1 or FIG. 5 having different arrangements of magnets; specifically multiple magnets arranged in an undefined configuration.
Figure 20B:
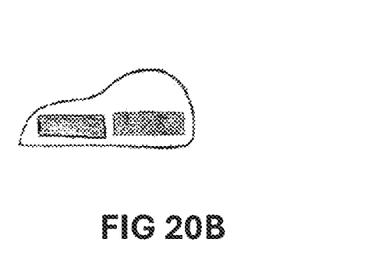
Figure 20C:
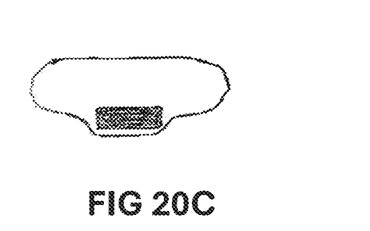

Referring to FIGS. 11A-17B, the surface of contact 112, 122 which defines the contact being made between the member and the tissue, can be, but need not be, planar. Other kinds of shapes, such as concave, convex, stepped or staircase-like can be contemplated. It will be convenient to note that the surface of contact of members placed at opposite sides of the tissue wall, such as members 11 and 12 in FIG. 2, and members 11 and 11' in FIG. 4, may have a complementary shape. By way of example, the shapes shown in FIGS. 13A-13B, 15A-15B and 17A-17B may be complementary. In another example, two mushroom-shaped members as shown in FIGS. 17A-17B may be used. These mushroom-shaped members may form plugs or anchors preventing the magnetically attached members to fall through the tissues once the tissue becomes necrotic and collapses.

Referring to FIGS. 7A-10C and FIGS. 18A-20C, the magnets 111, 121 or, as the case may be, magnetically active materials can have any suitable shape. They may be monolithic within the housing 110, or made up of separate parts arranged adjacent one another, as shown in FIGS. 19A-20C. Other shapes than disc or cylindrical are possible, such as ring, oval or parallelepiped.

Figure 21:
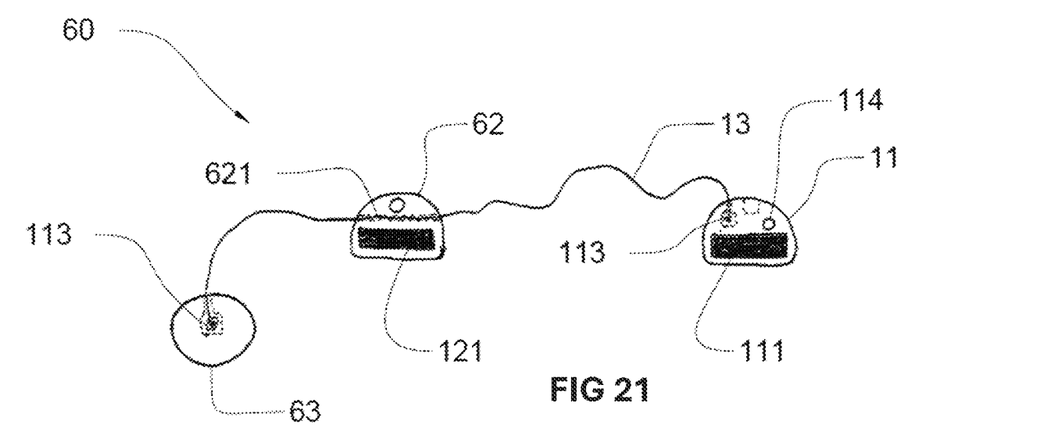
FIG. 21 illustrates an alternative embodiment of a device or assembly for pressure necrosis, in which tissue shearing is allowed to occur simultaneously with creating pressure necrosis.

It will be convenient to note that the shearing by the thread 13 can be facilitated by suitable selection of the mass (weight) of any of the members 11 and 12. Generally, a tension on the thread of at least 5 mm Hg may be sufficient for causing tissue shearing, with tensions of at least 10 mm Hg, at least 20 mm Hg, at least 50 mm Hg, or at least 100 mm Hg being advantageous. In some instances, it may be useful to maintain the thread 13 under a constant tension, as from the onset, particularly even prior to the collapse of the tissue due to pressure necrosis performed by the members 11 and 12. One possible way of accomplishing is by making one of the members slidable relative to the thread. Referring to FIG. 21, device 60 differs from device 10 in that the second member 62 is not fixedly attached to the thread 13, but is allowed to slide along the thread. The first member 11 is attached to one end of the thread 13, and a mass member 63 is attached to the opposite end of thread 13, with the second member 62 being slidingly attached to thread 13 in between the first member 11 and the mass member 63. To this end, the second member 62 comprises a through hole 621 slidingly receiving thread 13. Mass member 63 has a suitable weight in order to provide a desired tension in thread 13, but will advantageously not be magnetically attracted to either one of the members 62 and 11. In particular, mass member 63 may not comprise any magnet or magnetically active material. Mass member may have a mass at least equal to 50%, 75% or 100% of the mass of any one of the members 11 and 12. When members 11 and 62 are placed as shown in FIG. 2, the mass member 63 is freely suspended and will pull on the thread 13 and put it under tension to immediately start shearing tissue. It will therefore be clear that device 60 allows for simultaneous pressure necrosis and tissue shearing. A yet alternative embodiment is obtained by adapting the arrangement 10 of FIG. 1 to include the mass member 63 interposed between the first member 11 and the second member 12. In this case, mass member 63 may, but need not be slidingly attached to the thread 13.

Figure 22A:
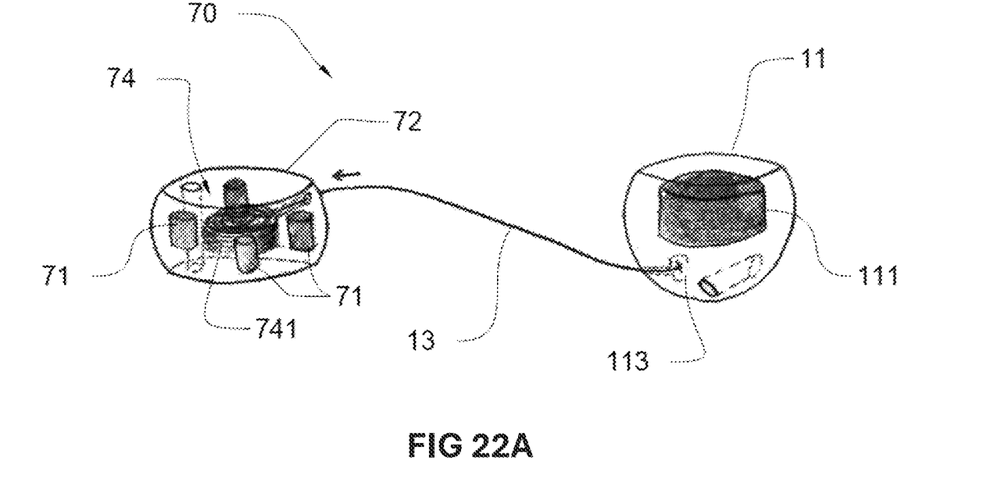
FIG. 22A illustrates a first of two alternative embodiments of the device of FIG. 21, which comprise a traction system (thread winding system) for loading the thread between the two members in order to maintain tension in the thread; specifically an embodiment in which the traction system is a spiral spring and magnets are placed around the spiral spring.
Figure 22B:
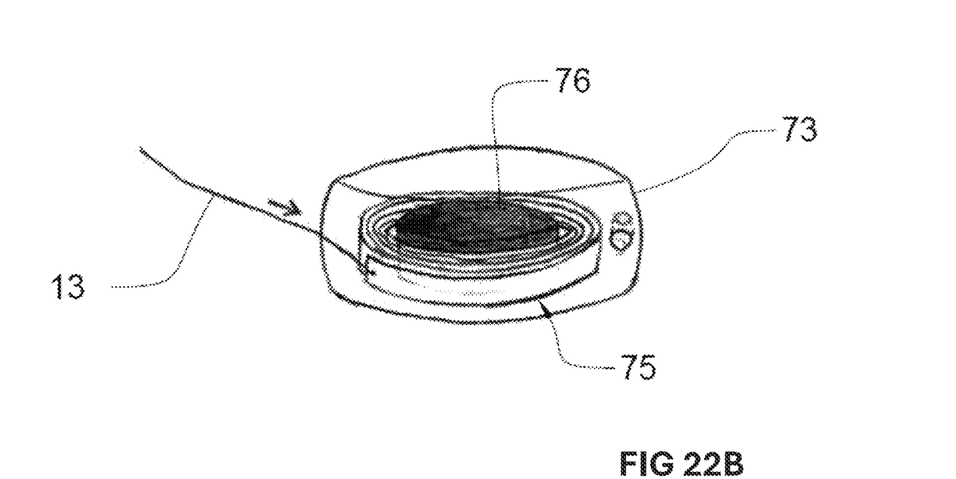
FIG. 22B illustrates a second of two alternative embodiments of the device of FIG. 21, which comprise a traction system (thread winding system) for loading the thread between the two members in order to maintain tension in the thread; specifically an alternative for the second member, wherein the spiral spring is coiled around a centrally placed magnet.

FIGS. 22A-B show alternative embodiments to the device 60, in which tension in the thread 13 is created through a thread winding system integrated within one of the members, or both. Referring to FIG. 22A, device 70 differs from device 10 in that the second member 72 comprises a thread winding system 74 for loading thread 13 in order to maintain tension in the thread. Thread winding system 74 can comprise a spiral spring 741 which is preloaded to pull on thread 13 according to a desired preload force acting in the direction of the arrow. Magnets 71 may be placed peripherally to thread winding system 74, as shown in FIG. 22A, or in any other suitable configuration. Referring to FIG. 22B, an alternative to FIG. 22A is shown, which differs from device 70 in that the thread winding system 75 in the second member 73 is a spiral spring which is coiled around magnet 76, i.e., spring 73 and magnet 76 are concentric. In an alternative embodiment, the arrangement of FIG. 21 is adapted to incorporate the thread winding system in the mass member 63.

Figure 23A:
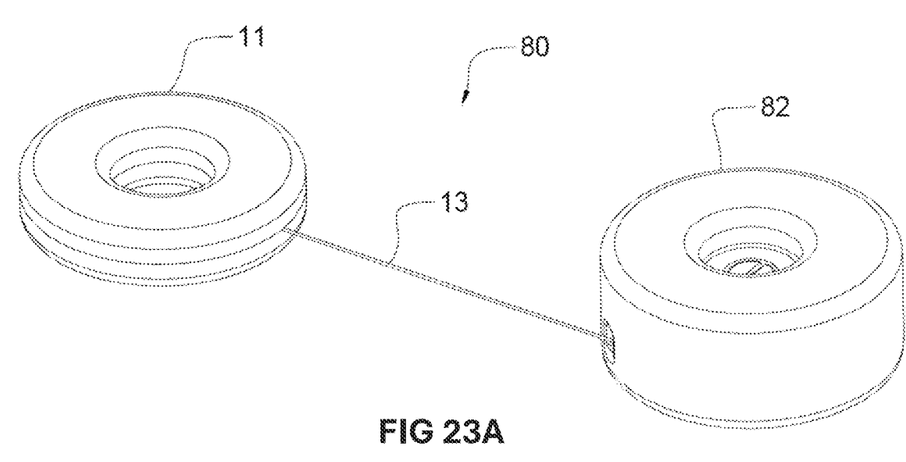
FIG. 23A illustrates a first of three views of an alternative embodiment of the devices of FIGS. 22A-B, wherein the magnet is arranged differently; specifically
Figure 23B:
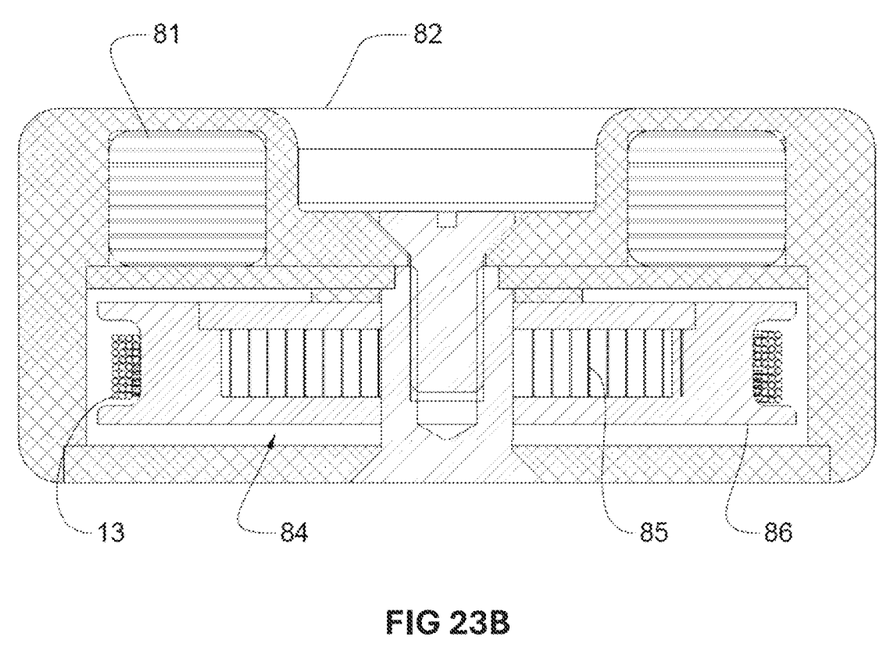
Figure 23C:
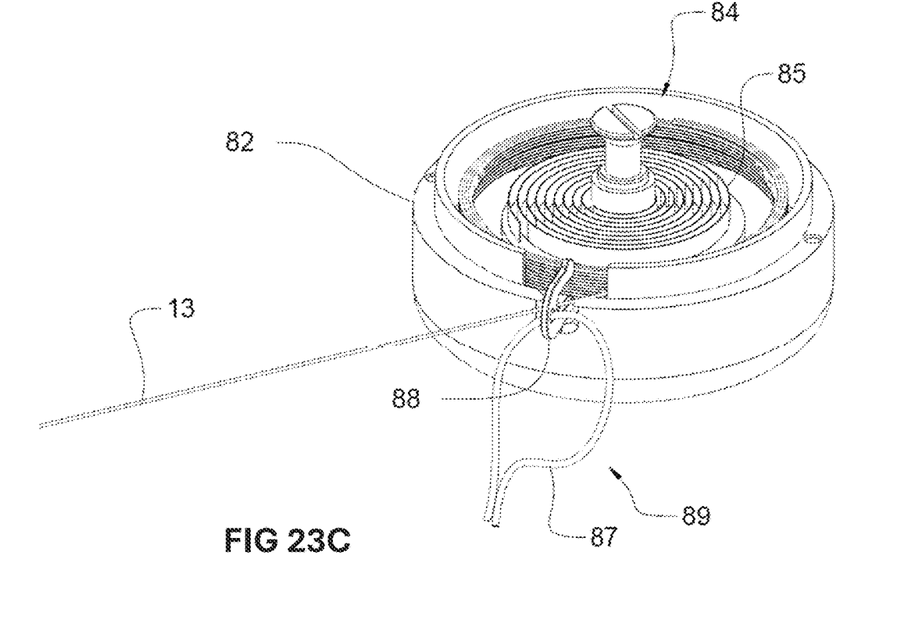
Figure 24:
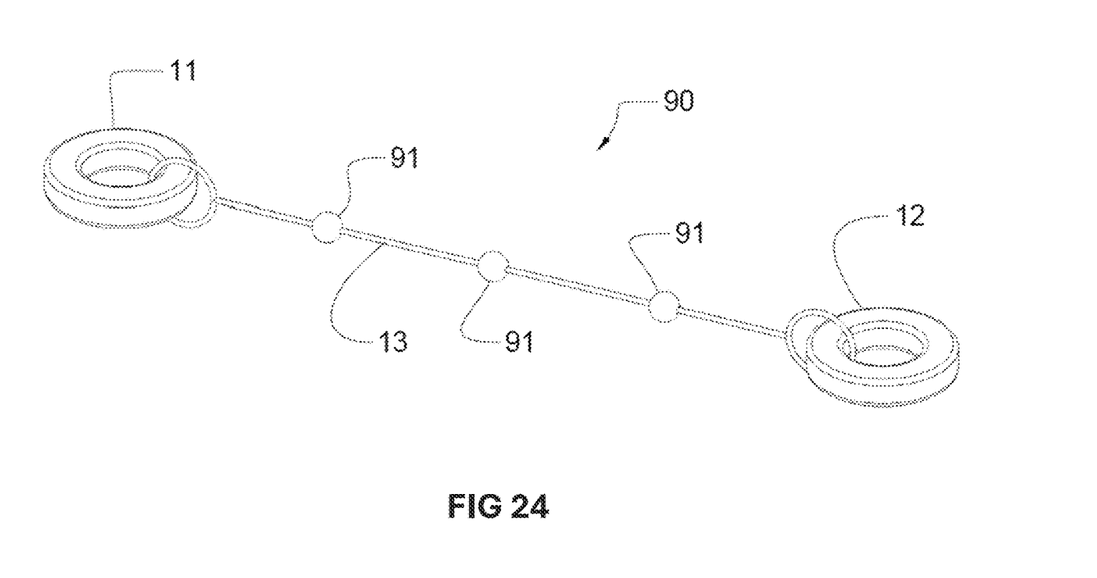
FIG. 24 illustrates another embodiment of device with an alternative means for pulling the thread towards the first and/or second member.

Yet an alternative embodiment to the devices 70 of FIGS. 22A-B is shown in FIGS. 23A-C, representing a device 80 comprising a thread winding system 84 incorporated in the second member 82. Device 80 differs from device 70 in the disposition of magnet 81 (see FIG. 23B) which is annular and arranged above or below the thread winding system 84. Alternatively, possibly annular magnets may be arranged above and below the thread winding system, e.g. in a symmetrical fashion. The thread winding system 84 comprises a spiral spring operably connected to a pulley 86. Thread 13 is wound on pulley 86. Spiral spring 85, or any other suitable spring, is advantageously preloaded to apply a suitable torque on pulley 86 to pull on thread 13. In the latter design, the thread winding system 84 and the magnet 81 can be kept separated from one another without interference.

Referring to FIG. 23C; a blocking system 89 can be provided in the second member 82 for blocking rotation of the thread winding system 84. By way of example, blocking system 89 comprises a blocking member 88 which blocks the pulley 86 and/or the spiral spring 85, e.g. by engagement. The blocking system 89 is releasable, e.g. by pulling on thread 87 attached to blocking member 88, the blocking member 88 is released and the pulley and spiral spring can turn and wind the thread 13.

Referring to FIG. 13, a yet alternative embodiment is shown, which differs from device 10 in that a plurality of third members 91 are attached along the thread 13, between the first member 11 and the second member 12. The third members may be arranged with advantageously uniform spacing between one another and they are advantageously fixed to thread 13. The third members advantageously show magnetic attraction to the first member 11 and/or the second member 12 and act here as thread pulling means. As the tissue is further sheared, the third member 91 closest to the first member 11 will progressively move to the first member due to the magnetic attraction. The third members 91 can have any suitable shape, e.g. beads, and advantageously have dimensions substantially smaller than those of the first member and second member, e.g. half or less of the size of the first member and/or second member. It will be convenient to note that neither the thread winding system in FIGS. 22A-B and 23A-C, nor the third members in FIG. 13 prejudice the position and shape of the magnet or magnetically active material, of the housing, or of the surface of contact, and these features may assume any suitable shape, e.g. as illustrated in FIGS. 7A-10C through 18A-20C.

Yet another alternative to the systems shown in FIG. 21 through 24 is to use an elastic or resilient thread to couple the members to one another. This thread is advantageously preloaded prior to placement of the device, e.g. by providing an appropriate structure which maintains the members at a distance larger than the length of the thread at rest, which structure is removed upon installing the device. The thread is stretched and thereby preloaded. In one example, the thread may be made of, or comprise a shape memory material. Suitable shape memory materials are shape memory polymers or (metal) alloys, which e.g. can retract at a body temperature level. One example is DiAPLEX® commercialised by Mitsubishi Corporation Fashion Co., Ltd., Japan. The use of a mass member pulling on the thread, of a traction system, or of elastic or resilient thread can be advantageously used in the application referred to in FIG. 4. That is, either one or both the devices 10 and 10' in FIG. 4 may be provided with means for (pre)loading the thread 13, 13'. In the example of FIG. 4, (pre)loading the threads 13, 13' with tensile stress enhances fusion between the tissues 42 and 43.

The thread is advantageously made of a non-resorbable material, and is advantageously a monofilament thread, e.g. made of polyamide. The shape of the housing 110 is advantageously atraumatic. While in the above embodiments, only one thread is described extending between the first member and the second member, it will be convenient to note that a plurality of such threads, e.g. two, three or more can be provided to extend between, and be connected to the first member and second member. The means for pulling the thread may be operable to pull some or all of these threads. Multiple threads advantageously allow for shearing tissue across multiple, spaced apart sections.

Each of the members has a diameter D (see FIG. 6B) or largest size advantageously smaller than or equal to 40 mm, advantageously smaller than or equal to 30 mm, advantageously smaller than or equal to 20 mm, advantageously smaller than or equal to 15 mm, advantageously smaller than or equal to 20 mm. The member 11 or 12 can have a diameter or size of at least 5 mm, advantageously at least 10 mm. The thread 13 extending between the members has a length which in an initial placement position is advantageously at least 80 mm, advantageously at least 100 mm, advantageously at least 120 mm. The mass of the member 11 or 12 generally depends on the application, and may be determined on the basis of e.g. contact length of the thread with the tissue in order to arrive at a desired tension on the thread.

Some aspects of the present invention as described herein are set out in the following numbered clauses.

A. Method of creating pressure necrosis of a tissue wall between a pouch and an adjacent cavity in a human or animal body, wherein the tissue wall comprises a periphery forming an edge of an opening between the pouch and the cavity, the method comprising:
  placing a first member into the pouch, such that the first member is adjacent the wall,
  placing a second member in the cavity and proximate the first member,
  wherein the first member and the second member comprise materials which magnetically attract one another,
  wherein the first member and the second member are placed such that there is magnetic attraction between the first member and the second member through the wall and wherein the first member and the second member compress an overlapping portion of the wall to create pressure necrosis,
  wherein the first member and the second member are connected through a thread, wherein the thread extends over the edge.

B. Method of clause A, wherein, following pressure necrosis, the first member and the second member are suspended by the thread forming a loop over the wall.

C. Method of clause B, wherein the thread shears the wall by action of a weight of the first and second members.

D. Method of clause B, wherein the thread shears the wall while the thread is under tension by action of a mechanism that induces a traction force in the thread.

E. Method of clause B, comprising exerting a pulling force on the thread while the thread shears the wall.

F. Method of clause B, wherein the wall is cut by the thread in a direction of gravity.

G. Method of clause A, wherein the thread does not pierce through the wall until pressure necrosis is created.

H. Method of clause A, wherein at least one of the first member and the second member comprises an encapsulated magnet.

I. Method of clause A, comprising inserting a delivery device having an internal lumen into the cavity, and
guiding the delivery device through the opening to the pouch and delivering the first member to the pouch by sliding the first member through the internal lumen;
delivering the second member to the cavity by sliding the second member through the internal lumen;
wherein the first member and the second member are connected by the thread in the internal lumen.

J. Method of clause A for treating diverticulum, wherein the pouch is a diverticulum.

K. Method of clause J, wherein the cavity is a segment of a gastrointestinal tract of the human or animal body.

L. Method of creating compression anastomosis between adjacent tissues, each of the tissues forming a wall of one of adjacent cavities of a human or animal body, the method comprising:
placing a first member and a second member in a first one of the adjacent cavities, proximate a first one of the walls, wherein the first member and the second member are spaced apart and connected to a first thread;
placing a third member and a fourth member in a second one of the adjacent cavities and proximate a second one of the walls, wherein the third member and the fourth member are connected to a second thread and are placed in correspondence of a respective one of the first member and the second member;
wherein the first, second, third and fourth members comprise materials which magnetically attract one another through the adjacent tissues to create pressure necrosis of an overlapping portion of the wall.

M. Method of clause L, wherein the first thread does not extend to the second one of the adjacent cavities upon placement of the first and second members and wherein the second thread does not extend to the first one of the adjacent cavities upon placement of the third and fourth members.

N. Method of clause L, comprising a step of shearing the adjacent tissues by the first thread or the second thread, wherein the shearing opens a lesion extending between a necrotic opening through the adjacent tissues formed at a location of the first member and a necrotic opening through the adjacent tissues formed at a location of the second member.

O. Method of clause N, wherein one of the first thread and the second thread shears the adjacent tissues while the respective thread is under tension by action of a mechanism that induces a traction force in the respective thread.

The invention claimed is:

1. A method of shearing a tissue wall between a first cavity and an adjacent second cavity in a human or animal body, the method comprising:
placing a first member into the first cavity, such that the first member is adjacent the tissue wall;
placing a second member in the second cavity and proximate the first member; and
positioning a thread connecting the first member and the second member such that the thread forms a loop from the first member to the second member around a peripheral edge of the tissue wall without passing through the tissue wall;
wherein the first member and the second member comprise materials which magnetically attract one another; and
wherein the first member and the second member are placed such that magnetic attraction between the first member and the second member through the tissue wall compresses an overlapping portion of the tissue wall to create pressure necrosis.

2. The method of claim 1, further comprising creating a compression anastomosis of a second portion of the tissue wall surrounding the overlapping portion.

3. The method of claim 1, wherein the second cavity communicates with the first cavity through a first opening, wherein the peripheral edge forms an edge of the first opening, and wherein following pressure necrosis, the first member and the second member create a second opening through the tissue wall between the first cavity and the second cavity distinct from the first opening, wherein the first member and the second member are suspended from the peripheral edge by the thread.

4. The method of claim 3, wherein the thread shears the tissue wall by action of a weight of the first and second members.

5. The method of claim 1, further comprising shearing the tissue wall using the thread while placing the thread under tension by action of a mechanism that induces a traction force in the thread.

6. The method of claim 1, further comprising exerting a pulling force on the thread such that the thread shears the tissue wall.

7. The method of claim 1, wherein the thread pierces through the tissue wall after pressure necrosis is created.

8. The method of claim 1, wherein at least one of the first member and the second member comprises an encapsulated magnet.

9. The method of claim 1, further comprising:
inserting a delivery device having an internal lumen into the second cavity;
guiding the delivery device through a first opening to the first cavity and delivering the first member to the first cavity by sliding the first member through the internal lumen; and
delivering the second member to the second cavity by sliding the second member through the internal lumen;
wherein the first member and the second member are connected by the thread in the internal lumen.

10. The method of claim 1, wherein the first cavity is a pouch which opens into the second cavity.

11. The method of claim 10 for treating diverticulum, wherein the pouch is a diverticulum.

12. The method of claim 10, wherein the second cavity is a segment of a gastrointestinal tract of the human or animal body.

13. The method of claim 1, wherein the first cavity and the second cavity are segments of a gastrointestinal tract of the human or animal body.

14. The method of claim 1, further comprising applying a continuing pressure on the tissue wall using the thread to cause shearing of the tissue wall from the peripheral edge toward the overlapping portion.

15. The method of claim 1, wherein the tissue wall comprises a septum.

16. A method of shearing a tissue wall between a first cavity and an adjacent second cavity in a human or animal body, the method comprising:
placing a first member into the first cavity, such that the first member is adjacent the tissue wall;
placing a second member in the second cavity opposite the first member;

positioning a thread connecting the first member and the second member such that the thread forms a loop from the first member to the second member around a peripheral edge of the tissue wall without passing through the tissue wall; and maintaining a tension on the thread by reducing a length of the loop to apply a pressure on the tissue wall which causes shearing of the tissue wall from the peripheral edge towards the first member and the second member;

wherein the first member and the second member are magnetically attracted to each other, and are placed such that magnetic attraction between the first and the second members through the tissue wall causes a compression of a portion of the tissue wall to create pressure necrosis.

17. The method of claim 16, wherein maintaining a tension on the thread comprises using a thread winding mechanism.

18. The method of claim 17, wherein maintaining the tension includes maintaining the tension using a spring.

19. The method of claim 16, wherein the first member comprises an encapsulated magnet.

20. The method of claim 16, further comprising:

inserting a delivery device having an internal lumen into the second cavity;

guiding the delivery device through a first opening to the first cavity and delivering the first member to the first cavity by sliding the first member through the internal lumen; and delivering the second member to the second cavity by sliding the second member through the internal lumen;

wherein the first member and the second member are connected by the thread in the internal lumen.

* * * * *